United States Patent [19]

Nestor et al.

[11] 4,210,145
[45] Jul. 1, 1980

[54] SURGICAL HOLE CUTTER FOR SQUARE HAIR TRANSPLANT PLUGS

[75] Inventors: Jack Nestor, Miami Beach; John W. Devine, Jr., Miami, both of Fla.

[73] Assignee: Nestor Engineering Associates, Inc., Miami, Fla.

[21] Appl. No.: 893,626

[22] Filed: Apr. 5, 1978

[51] Int. Cl.² .............................................. A61B 17/32
[52] U.S. Cl. ................................... 128/305; 128/310
[58] Field of Search ................ 30/113.1, 279 R, 305, 30/304, 276, 358, 366, 353, 346; 408/227, 231, 233, 204, 206; 128/305, 314, 315, 213, 330, 310, 749, 751, 753, 754, 355; 175/416, 421, 413; 172/19

[56] References Cited

U.S. PATENT DOCUMENTS

| | | | |
|---|---|---|---|
| 1,390,720 | 9/1921 | Powers | 128/305 |
| 1,739,214 | 12/1929 | Darling | 30/304 |
| 1,858,040 | 5/1932 | Jarnette | 30/358 |
| 3,683,892 | 8/1972 | Harris | 128/305 X |

FOREIGN PATENT DOCUMENTS

| | | | |
|---|---|---|---|
| 289050 | 7/1966 | Australia | 172/19 |
| 1072361 | 9/1954 | France | 128/314 |
| 1334383 | 10/1973 | United Kingdom | 30/304 |

*Primary Examiner*—William E. Kamm
*Assistant Examiner*—Michael H. Thaler
*Attorney, Agent, or Firm*—Erwin M. Barnett

[57] ABSTRACT

A surgical cutter for preparing recipient sites for square scalp plugs in hair transplanting has four disposable blades removably attached to the four longitudinal sides of a core having a square cross-section of predetermined dimensions corresponding to the width of each blade and to the area at the surface of the hole to be excised. Each blade projects a predetermined distance beyond the end of the core equivalent to the required depth of cut and has a sharpened inclined cutting end edge extending from a point located at one side edge inwardly to the opposite side edge in guillotine fashion. The side of the blade adjacent the point is also a sharpened cutting edge extending inwardly therefrom. One blade point is located in each corner of the square projecting from the recessed side of the adjacent blade whereby the side cutting edges are operatively exposed for cutting a subdermal portion of the scalp on rotation of the core approximately 1/4 turn after the square has been cut by the inclined end cutting edges of the blades. A handle removably accommodates the cutter in operative position and in a reverse blade protective position for handling during sterilization.

9 Claims, 8 Drawing Figures

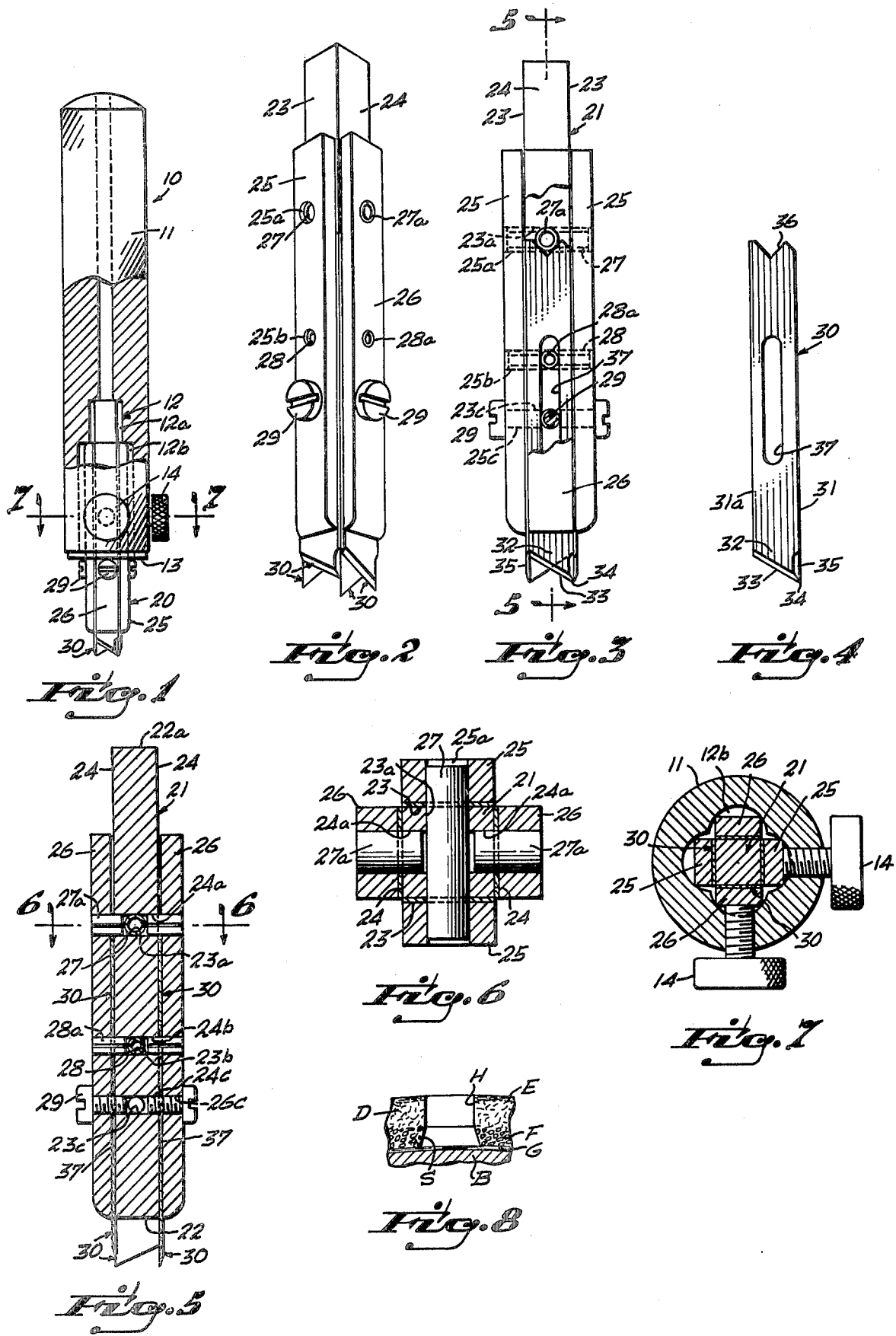

SURGICAL HOLE CUTTER FOR SQUARE HAIR TRANSPLANT PLUGS

BACKGROUND OF THE INVENTION

1. Field of the Invention

This invention relates to a surgical cutting instrument and particularly to a cutter having four disposable and replaceable blades arranged for excising square plugs from a recipient area of the scalp preparatory to receiving square donor plugs in hair transplant surgery, each blade having two cutting edges, one edge disposed in guillotine fashion to facilitate the initial downward axial cut, the other edge coactingly providing a sharp point and means for effecting a sideward rotational cut.

2. Description of the Prior Art

The current preferred technique of hair transplant surgery utilizes the removal of a strip graft from the donor area which, when closed, leaves only a linear scar. In the recipient area, strip grafts may be used to establish the hair line while plug grafts, originally cylindrical, that is circular in cross-section, were used behind the hair line. On the recipient site, the plug grafting is performed in several steps utilizing a staggered or spaced pattern and then filling in between previous grafts at a later date. This allows for preservation of the blood circulation and results in denser growth of hair from each of the plug grafts. Formerly, in preparing the recipient sites, cylindrical plugs were removed by a rotating circular cutter which provided cylindrical holes for correspondingly sized donor plugs which may be removed from the donor sites in a similar manner.

It was then suggested that the donor strips be also used as a source of plug grafts by cutting the strips into squares thereby enabling substantially all the hair follicles removed as strips from the donor site to be utilized as square plugs which provide about 25% more hair for the recipient site than circular plugs of equivalent diameter. The preparation of the recipient site to receive the square donor plugs requires the removal of scalp to form square, that is, substantially hexahedral, holes having predetermined dimensions cut to relatively close tolerances. A square shaped cutter of the conventional cookie or die cutter variety, which is inherently difficult to maintain in a sharpened condition, has proved to be totally ineffective and impractical for this purpose, in that an excessive amount of force must be applied to achieve the required depth of cut and, when so accomplished, the cut fails to be sufficiently sharp and clean, which is a desirable factor in promoting healing. There is, therefore, an urgent need for a practical, efficient, easy to use, instrument for cutting these square holes in the recipient area of the scalp which will overcome the above mentioned problems and achieve satisfactory results so that the advantages of the square plug technique may be realized.

SUMMARY OF THE INVENTION

Among the objects of the invention is to provide a surgical cutter for preparing recipient sites for square, that is, substantially hexahedral, hair graft donor plugs which shall meet the needs hereinbefore described as an effective cutter capable of forming holes in the scalp, each having sharp and clean cut walls defining a precise square upper portion slightly smaller in surface area than that of the donor plug and a circular bottom portion of a diameter equal to the diagonal of the inscribed square upper portion into which the bottom portion of the donor plug may expand.

The invention features a cutter comprising four similar elongated flat blades of predetermined width corresponding to the width of the sides of the square upper portion of the recipient hole to be cut in the scalp and a supporting prism-shaped core of square cross-section also sized to correspond to the upper portion of the hole and providing four longitudinal sides along which the blades are mounted to project from one end thereof a distance defining the depth of cut. The projecting end edge of each blade is inclined inwardly in guillotine fashion from a point formed along one longitudinal side of the blade providing a recess or cutback along the opposite longitudinal side of predetermined length which is shorter than the depth of cut. The inclined end edge and an end portion of the longitudinal side adjacent the point of each blade are sharpened. Means precisely mount each blade individually for easy removal and replacement along a longitudinal side of the core to project from the end thereof for the predetermined depth of cut. The blades are arranged about the core to locate one point in each corner of the square, the recess of one blade exposing the sharpened longitudinal edge portion of the adjacent blade for cutting a bottom section of hole by axial rotation of the core after the inclined edges complete their cut to the predetermined depth. The cutter removably fits into an axial bore of a handle with the blades extending in operative position for manipulation thereby, or alternatively, the cutter may be reversed in the handle for protecting the sharpened blades during sterilization or when not in use.

BRIEF DESCRIPTION OF THE DRAWING

FIG. 1 is an elevational view of the surgical cutter mounted in the handle ready for surgery in accordance with the invention.

FIG. 2 is an enlarged perspective view of the surgical cutter embodying the invention removed from the handle in FIG. 1 and showing the arrangement of the cutting edges of each of the blades with respect to each other.

FIG. 3 is a side elevational view of the cutter shown in FIG. 2 with parts broken away to show details of the means for locating and removably attaching the blades to the core.

FIG. 4 is an elevational view of one of the blades embodying the invention detached from the core.

FIG. 5 is a longitudinal section of the cutter taken on line 5—5 in FIG. 3.

FIG. 6 is a transverse section of the cutter taken on line 6—6 in FIG. 5.

FIG. 7 is a transverse sectional view of the cutter and handle taken on line 7—7 in FIG. 1, and FIG. 8 is a section taken perpendicular to the surface of the scalp through the center of a recipient hole cut by the cutter embodying the invention showing the upper square portion and the lower circular portion of the hole which has sloping side walls between the corners of the square, the section being taken parallel to one pair of the square sides.

DESCRIPTION OF THE PREFERRED EMBODIMENT

Referring in detail to the drawing, 10 generally denotes a surgical instrument for preparing holes H, as illustrated in FIG. 8, in the recipient area of a patient's scalp for transplanting therein hexahedral donor hair bearing plugs removed from the patient's donor areas of the scalp and prepared for implanting in holes H in accordance with the most recent surgical procedures and hair transplanting technique. Surgical instrument 10 includes a cylindrical handle 11 sized for easy gripping and formed to detachably mount cutter 20, the latter being made of suitable non-corrosive metal, such as, surgical stainless steel or the like, while handle 11 may be made of aluminum. Cutter 20 contemplates providing a square knife having four similar sides each formed with a bottom edge sharpened for cutting and inclined inwardly, that is, upwardly as seen in FIG. 2, from a point located at one corner of the square to the adjacent corner and exposing the downwardly extending edge of the adjacent side of the square which is also sharpened for cutting in the manner and for the purpose hereinafter described.

As shown herein, cutter 20 comprises a prism-shaped core 21 having square forward and rearward ends 22 and 22a, respectively, and four longitudinally extending rectangular shaped sides 23, 24 against which four similar flat blades 30 are replaceably secured with end portions 32 thereof extending a predetermined distance beyond forward end 22 forming the square knife embodying the invention. Blade retaining plates 25, 26 overlie blades 30 and are individually removably retained in assembly on core 21 by screws 29.

As best seen in FIGS. 3 and 4, each of the four blades 30 has opposite parallel longitudinal sides 31 and 31a and at one end portion 32 thereof terminates in an inclined sharpened end edge 33 extending inwardly from point 34 located at longitudinal side 31 to the opposite longitudinal side 31a. A sharpened edge 35 also extends along an end portion of longitudinal side 31 inwardly from point 34 a distance substantially equal to the cutback of longitudinal side 31a by the incline of edge 33. The opposite end of blade 30 may be formed with a centrally located V-shaped notch 36 and a midportion of blade 30 may have a longitudinally extending central slot 37.

In addition to screws 29, suitable locating and registering means are provided to coact between the rectangular sides 23, 24 of core 21 and retaining plates 24, 25 to longitudinally align the latter and blades 30 along sides 23, 24 and to axially position blades 30 for controlling the distance each blade portion 32 projects beyond core end 22 to accurately define the depth of cut.

To achieve these purposes, core 21 has three perpendicular pairs of transverse bores 23a, 24a, 23b, 24b and 23c, 24c drilled therethrough. Bores 23a, 23b and 23c extend between one pair of opposite longitudinal sides 23, and bores 24a, 24b and 24c, which intersect bores 23a, 23b and 23c, respectively, at the longitudinal axis of core 21, extend between the other pair of opposite longitudinal sides 24. Suitable pins, herein shown as roll pins 27 and 28 are press fitted into bores 23a and 23b, respectively, and are sized to extend beyond each opposite side 23, the latter characterized as male, for engaging blades 30 and blade retaining plates 25. The latter, being characterized as female, are each formed with openings 25a, 25b and 25c extending therethrough and located to register with bores 23a, 23b and 23c. Pins 27 and 28, having opposite ends projecting to engage openings 25a and 25b, respectively, extend through bores 23a and 23b thereby bisecting bores 24a and 24b, respectively, into openings extending inwardly from opposite longitudinal sides 24, the latter being characterized as female. Relatively short pins 27a and 28a, which may also be of the roll pin type, are mounted in suitable openings in blade retaining plates 26, the latter being characterized as male. Pins 27a and 28a project from plates 26 to register with and engage bores 24a and 24b, respectively, as seen in FIGS. 5 and 6. Bores 23c and 24c are suitably threaded for engagement by screws 29 extending through openings 25c and 26c in blade retaining plates 25 and 26, respectively. Pins 27 and 27a are located with respect to forward end 22 of core 21 to serve as positioning and stop means for blades 30 by engaging V-shaped notches 36 thereof so that end portions 32 project beyond forward end 22 the predetermined distance equal to the desired depth of cut. The forward ends of blade retaining plates 25 and 26 align with forward end 22 and coact therewith by providing additional contact area with the surface of the scalp in limiting the depth of cut. Pins 28 and 28a, serving as aligning means, and screws 29, serving as removable securing means, are located and diametrically sized to pass through central slots 37 in blades 30.

Handle 11, as seen in FIGS. 1 and 7, is formed with an axial bore 12 having an intermediate size enlargement 12a at a midportion thereof and a large size enlargement 12b extending from enlargement 12a to communicate with forward end 13 from which cutter 20 projects when mounted in operative position. Enlargement 12a is proportioned to accommodate the end of core 21 extending rearwardly beyond blade retaining plates 25 and 26. Enlargement 12b is shaped and sized to coaxially accommodate core 21 with its blades 30 and blade retaining plates 25 and 26 in assembled position whereby thumb screws 14, which are mounted in perpendicular relation to each other in suitable threaded openings in handle 11 adjacent forward end 13, engage the flat exterior surfaces of adjacent blade retaining plates 25 and 26. This perpendicular arrangement of thumb screws 14 provides double protection against cutter 20 becoming loose when in use and also, by coaction of each thumb screw 14 with the opposite wall portion of bore 12b, pressure is applied radially inwardly on each pair of opposite blade retaining plates 25 and 26 clamping their respective blades therebetween and providing an auxiliary means for retaining blades 30 and their projecting portions 32 in proper aligned relation comprising the square knife in the event one or more of the screws 29 are not sufficiently tightened. The surface of handle 11 may be suitably knurled for improved hand gripping.

The practical utility and operation of surgical instrument 10 will now be apparent. Cutter 20, assembled as shown in FIG. 2, is inserted into bore enlargement 12b of handle 11 blade end first, that is, opposite to the position shown in FIG. 1, to the full extent as limited by screws 29 contacting end 13. Thumb screws 14 are then tightened to retain cutter 20 in its fully inserted, reverse position wherein blade points 34 and sharpened edges 33 and 35 extend short of the inner, narrowing end of bore enlargement 12b and are protected for storage and while sterilizing instrument 10.

After sterilization, and prior to removal of cutter 20 from handle 11, the exposed rearward end 22a of core 21 may be dipped into a suitable dye and utilized as a marker for laying out the pattern, positions and orientation of the square holes to be cut in the recipient area of the patient's scalp.

When ready for surgery, thumb screws 14 are loosened, cutter 20 reversed in handle 11 and inserted to the fully retracted position shown in FIG. 1 wherein rearward end 22a of core 21 abuts the inner end of intermediate enlargement 12a, and cutter 20 is secured in position by retightening thumb screws 14.

The hair transplant procedure contemplates cutting the donor strips into hexahedral plugs, which may be slightly oblique to conform to the angle of the hair follicles and are slightly larger in cross-sectional area than that of the upper square portion of hole H. For example, where blades 30 have a width of 5 mm to cut a hole 5 mm square at the surface of the scalp, the donor plug is cut to a 5.5 mm square. Hole H is prepared by aligning blades 30 with a dye marked square on the recipient area of the scalp and pressing downwardly so that points 34 and inclined edges 33 cut through the epidermis E, the dermis D, the layer of subcutaneous fat F, until limited by the forward end 22 of core 21 and the forward ends of blade retaining plates 25 and 26. In this position, blade points 34 will have reached approximately the level of the galea G which covers the underlying bone B of the skull and a precise square incision will have been made extending from the surface of the scalp, which now contacts forward end 22 of core 21, to the recessed end of inclined edges 33 at longitudinal sides 31a of blades 30. Cutter 20 is then axially rotated through an arc slightly in excess of 90° whereby edges 35 cut a circular incision at the bottom portion in hole H while the four straight walls formed by the square incision in the upper portion of hole H are deflected by compression of the surrounding tissue to permit this rotation. When using cutter 20 having sharpened edges 33 and 35 disposed as shown herein, the rotation is in a counterclockwise direction. Cutter 20 is then withdrawn, the tissue assuming its normal configuration, and the plug is removed by cutting the center stalk thereof at the bottom in accordance with well known surgical procedure. The remaining hole H has a contour substantially as shown in FIG. 8, that is, having a square upper portion which is in an inscribed relation to the circular bottom portion. The circular incision cut by edges 35 to extend between the corners of the square form sidewalls S which slope from the straight line bottom of the square upper portion of hole H to the circular bottom thereof. The donor plug is then implanted in hole H with its upper portion snugly engaging the square walls of the upper portion of hole H and the bottom portion of the plug being permitted to expand slightly into the larger area of the circular bottom portion of hole H thereby reducing the likelihood of the donor plug being expelled.

After continued use, blades 30 may be removed from core 21, preferably one at a time, and replaced with new, sharp blades. This is accomplished with the aid of a small screwdriver by removing screws 29 so that blade retaining plates 25 and 26 will separate from their respective longitudinal sides 23 and 24. Separation may be facilitated by inserting the screwdriver blade under the rearward end of plates 25 and 26 into the space formed by the thickness of blades 30, as will be clear from FIGS. 3 and 5, and gently prying plates 25 and 26 away from core 21. When changing blades 30 on male longitudinal sides 23 of core 21, after the old blade 30 is removed, the new blade is properly positioned on male side 23 with notch 36 engaging pin 27 and pin 28 extending through slot 37. Female blade retaining plate 25 is then readily positioned on new blade 30 with pins 27 and 28 engaging openings 25a and 25b, respectively, and screw 29 is replaced and tightened. When changing blades 30 on female longitudinal sides 24 of core 21, after the old blade 30 is removed, the new blade may be positioned with its outfacing surface against male blade retaining plate 26 with notch 36 engaging pin 27a and pin 28a extending through slot 37. With new blade 30 held in position thereagainst, male blade retaining plate 26 is then mounted on female longitudinal side 24 by inserting pins 27a and 28a into bores 24a and 24b, respectively, and screw 29 is replaced and tightened.

When core 21 is made in a smaller cross-sectional size, as for example, 3.5 mm square, with blades 30 of corresponding width to cut a smaller square hole H, bores 23c and 24c may be axially offset with respect to each other rather than intersecting as shown in FIG. 5, thereby providing a maximum distance of ½ the length of the respective bore to accommodate each of the screws 29. Likewise, openings 25c in female blade retaining plates 25 are positioned to align with bores 23c and openings 26c in male blade retaining plates 26 are positioned to align with bore 24c.

The surgical knife for preparing recipient holes in the patient's scalp for implanting therein square donor plugs herein disclosed is seen to achieve the several objects of the invention and to be well adapted to meet conditions of practical use. As various possible embodiments might be made in this invention, and as various changes might be made in the disclosed instrument, it is to be understood that all matter herein set forth or shown in the accompanying drawing is to be interpreted as illustrative and not in a limiting sense.

What is claimed is:

1. An instrument for cutting a hole in the scalp for receiving a hair transplant donor plug of square surface area comprising a handle having a longitudinal axis, said handle terminating at one end in a coaxially mounted square knife having four identical sides, each side being formed with a bottom edge sharpened for cutting and inclined inwardly from a point located at one corner of the square to a cutback at the adjacent corner of the square, each point having an adjacent edge extending parallel to said longitudinal axis sharpened for cutting and extending inwardly along a corner of the square and being exposed by said cutback, the interior of the square knife being recessed a predetermined distance inwardly of said points and of said cutbacks as a depth of cut limiting means, said inclined sharpened edges cutting a square incision on axial pressure of said handle to said depth of cut and said sharpened adjacent edges cutting a circular incision at the bottom of said square incision upon rotation of said handle.

2. A surgical knife assembly for cutting a square hole having a circular bottom comprising a prism shaped core having a longitudinal axis and four longitudinally extending sides and a square end, four flat blades conforming in width to said sides of the core, individual means removably mounting each of said blades against one of said sides with an end portion of each blade having opposite side edges extending parallel to said longitudinal axis projecting a predetermined distance beyond said square end, the projecting end portion of each blade having a sharpened end edge coacting with the other sharpened blade edges to cut a square incision on application of axial pressure to said core, said sharpened end edge of each of the blades being inclined in guillotine fashion providing a point located at one corner of the square defined by said blades, the side edge adjacent each point being sharpened for cutting a circular incision providing said circular bottom below said square incision on rotation of said assembly.

3. A surgical knife assembly for cutting a square hole comprising a prism shaped core having four longitudinally extending sides and opposite square ends, four flat blades conforming in width to said sides of the core, individual means removably mounting each of said blades against one of said sides with an end portion of each blade projecting a predetermined distance beyond a first of said core ends, the projecting end portion of each blade having a sharpened end edge coacting with the other sharpened blade edges to cut a square incision on application of axial pressure to said core, said individual mounting means for each of said blades comprising a plate overlying the blade and conforming thereto in width, registering pin means extending between said core and plate, and a removable screw spaced from said pin means extending through openings in the blade and plate and threaded into the core, said blade having an opposite end engaging said pin means as a stop defining said projecting predetermined distance and preventing relative axial movement of the blade on application of said axial pressure.

4. A surgical knife assembly for cutting a square hole comprising a prism shaped core having four longitudinally extending sides and opposite square ends, four flat blades conforming in width to said sides of the core, individual means removably mounting each of said blades against one of said sides with an end portion of each blade projecting a predetermined distance beyond a first of said core ends, the projecting end portion of each blade having a sharpened end edge coacting with the other sharpened blade edges to cut a square incision on application of axial pressure to said core, said individual mounting means for each of said blades including a plate overlying the blade and conforming thereto in width, said core being formed with a pair of transverse intersecting bores, each transverse bore extending between an opposite pair of said longitudinal sides of the core, a pin extending through a first of said transverse bores and projecting from a first pair of said core longitudinal sides and bisecting the second of said transverse bores into an opening in each of said second pair of core longitudinal sides, each of said plates overlying said first pair of core longitudinal sides being formed with an opening engaging said pin, each of said plates overlying said second pair of core longitudinal sides mounting a second pin engaging said opening, each of said blades having an opening through which said first and second pins extend.

5. The surgical knife assembly defined in claim 4 in which said individual mounting means include a removable screw spaced from said first and second pins and extending through openings in each of said blades and each of said plates and threaded into said core, and each of said first and second pins being roll pins.

6. A surgical knife assembly for cutting a square hole comprising a prism shaped core having four longitudinally extending sides and opposite square ends, four flat blades conforming in width to said sides of the core, individual means removably mounting each of said blades against one of said sides with an end portion of each blade projecting a predetermined distance beyond a first of said core ends, the projecting end portion of each blade having a sharpened end edge coacting with the other sharpened blade edges to cut a square incision on application of axial pressure to said core, said individual mounting means for each of said blades including a plate overlying the blade and conforming thereto in width and a removable screw threaded into the core and extending through openings in the blade and plate, the other of said core ends projecting beyond said plates, a separable handle substantially cylindrical in shape, an axial bore enlargement of predetermined length formed in the handle to extend from an opening at one end of the handle inwardly to a narrowing interior end, said bore enlargement having a cross-sectional size and shape to telescopingly mount said surgical knife assembly therein with said first core end projecting beyond said end of the handle when the other end of the core abuts said narrowing interior end, and thumb screw means mounted in the handle adjacent said open end to radially extend into said axial bore enlargement and engage said knife assembly for releasably locking the latter in said telescoped position.

7. The surgical knife assembly defined in claim 6 in which said thumb screw means includes a pair of thumb screws extending in perpendicular relation to each other, said axial bore enlargement cross-section being shaped to position said surgical knife assembly in said telescoped position to diametrically align each pair of opposite plates with one of said thumb screws whereby radially inward pressure is exerted on each pair of opposite plates by one of the thumb screws serving as auxiliary means cooperating with said removable screws to retain each of said blades in alignment against its respective longitudinal side of the core.

8. The surgical knife assembly defined in claim 6 in which said removable screws have heads projecting from said plates beyond said bore enlargement cross-section, said knife assembly being selectively reversible in said handle axial bore enlargement, said screw heads being located a predetermined distance from said core first end to contact said handle end as stop means for limiting the telescoping of the knife assembly into the bore enlargement when in a reversed position to locate said sharpened blade edges within said bore enlargement and beyond said thumb screw means and short of said narrowing interior end as protection against damage during sterilization and storage.

9. An instrument for cutting a hole in the scalp for receiving a hair transplant donor plug of square surface area comprising four similar flat blades of predetermined width, each blade having opposite longitudinal side edges and a sharpened end edge inclined inwardly from a point at a first of said side edges to the other side edge at an angle to provide a recess along said other side edge of a first predetermined distance, a prismatic core of square cross-section having a longitudinal axis and four longitudinal sides, each of a width corresponding to said blade width, means for removably mounting one of said blades along each of said core sides with said blade point projecting a second predetermined distance beyond a first end of said core, said second distance defining the depth of cut and being in excess of said first predetermined distance, said four blades defining a square configuration to be cut by the instrument with one of said points located in each corner of the square adjacent to the recess of an adjacent blade exposing an end portion of each of said first longitudinal side edges, each of said exposed end portions extending parallel to said core longitudinal axis and being sharpened for cutting a circular bottom section of said hole by axial rotation of the core after said sharpened inclined end edges complete their cut to said predetermined depth.

* * * * *